United States Patent [19]

McRae

[11] Patent Number: Plant 5,979

[45] Date of Patent: May 12, 1987

[54] ASIATIC LILY NAMED POLLYANNA

[75] Inventor: Edward A. McRae, Boring, Oreg.

[73] Assignee: Melridge Inc., Gresham, Oreg.

[21] Appl. No.: 710,427

[22] Filed: Mar. 11, 1985

[51] Int. Cl.[4] ..... A01H 5/00

[52] U.S. Cl. ..... Plt./68

[58] Field of Search ..... Plt./68

*Primary Examiner*—James R. Feyrer

*Attorney, Agent, or Firm*—Charles W. Rummler; John B. Lungmus

[57] ABSTRACT

A new variety of Asiatic hybrid lily having large sized flowers of excellent form borne on a single stem in a compact raceme and particularly characterized by their unusual combination of yellow and gold color tones and by their widely spaced maculation, which extends across the base of the tepals, particularly the petals, from each side of the end portion of the nectary, providing a color pattern that is new in the upright Asiatic division of lilies. The flowers have a long persistence both on the plant and as cut-flowers and the plant itself is an excellent garden plant highly resistant to disease and showing high tolerance to virus. Its bulbs may be precooled and forced for cut-flower production and its flowers are produced in midseason, inbetween the flowering times of its siblings of similar appearance, so that it extends the season of cut-flower production.

1 Drawing Figure

BACKGROUND OF THE INVENTION

This new variety of lily plant originated as a seedling selected from a group of seedlings resulting from my crossing of the species *Lilium wilsonii* var. '*flavum*' and the cultivar Connecticut King at Sandy, Oreg., in the course of breeding efforts carried on by me since 1971 with the object of producing superior upright-flowering Asiatic lilies in shades of yellow and gold and suited to cut-flower production in a range of flowering times which would extend the cut-flower season. This seedling was selected for propagation because of the large size of its flowers, which have petals of thick texture and an unusual tepal color pattern, each yellow tepal being flushed with gold over its inner half and the rear portion of each petal, on each side of its nectary, is covered with medium to large-sized deep magenta spots. This selected seedling has been asexually reproduced by me and under my direction at Sandy, Oreg., and successive generations produced by bulb-scale propagation and natural propagation from bulblets has shown that the clone is vigorous and a good grower and propagator, having desirable characteristics of hybrid vigor, great hardiness, and a high degree of disease resistance, as well as all of the desired characteristics of form, color, and habit. These successive generations have also demonstrated that the novel and distinctive characteristics of this new variety hold true under asexual propagation from generation to generation and appear to be firmly fixed.

DESCRIPTION OF THE DRAWING

My new variety of lily plant is illustrated in the accompanying photographic drawing, which shows a three-fourth face view of an open bloom, together with several buds in various stages of growth, and illustrates the flowwr form and tepal shape and arrangement, the view having been hand-painted to show in particular the novel and distinctive yellow and gold pattern and its heavy maculation.

DESCRIPTION OF THE NEW VARIETY

The following is a detailed description of this new variety of Asiatic hybrid lily with the color designations according to The R.H.S. Colour Chart published by The Royal Horticultural Society of London, England, and with nomenclature according to The International Lily Register and The Royal Horticultural Society.

THE PLANT

Origin: Seedling.

Parentage:

*Seed parent.*—*Lilium wilsonii* var. '*flavum*' (unpatented).

*Pollen parent.*—"Connecticut King" (unpatented).

Classification:

*Horticultural.*—Hybrid lily cultivar, Division I-A of the Horticultural Classification of Lilies by The Royal Horticultural Society.

*Commercial.*—Upright Asiatic hybrid lily.

Form: Single stem, erect, and stately.

Height: About 120 to 170 cm. from bulbs of about 15 to 20 cm. in circumference.

Growth: Vigorous and upright.

Foliage:

*Form of growth.*—Sessile.

*Quantity.*—Abundant.

*Leaf size.*—About 8 to 12 cm. long and about 1.5 to 2 cm. wide at the base.

*Leaf shape.*—Lanceolate.

*Texture.*—Leathery.

*Aspect.*—Glossy.

*Color.*—Medium green.

Bulbs:

*Size.*—Ranging to about 25 cm. in circumference in commercial use.

*Color.*—White.

THE BUD

Form: Ovoid to long ovoid with obtuse ends.

Size: About 7 to 9 cm. long just prior to opening.

Opening rate: The bud opens slowly at maturity in about one hour in response to light.

Color: Medium to deep yellow when the sepals first divide and also when the tepals begin to unfurl.

Peduncle:

*Length.*—About 7 to 10 cm. depending upon light levels.

*Color.*—Medium green.

THE FLOWER

Blooming habit: Annually, in midseason for Asiatic lilies. October-dug bulbs, properly cooled and planted in February under glass in western Oregon and with no supplementary lighting, flower in an average of 85 to 90 days.

Size: Large; about 15 to 18 cm. in diameter.

Borne: As a raceme with about 5 to 8 buds and flowers on a single stem.

Shape: Generally flat but slightly dished with tepals widely spaced angularly and having lightly recurved tips.

Tepalage:

*Number.*—Six.

*Arrangement.*—Hexagonal with petals angulated sixty degrees from and above the sepals.

*Shape.*—Generally ovate petals with broad mid-portion and acuminate end portion. Sepals are more slender.

*Color.*—The base color is Yellow, R.H.S 12 A-B, and each tepal has a flush of Gold, R.H.S. 21A, about 2 cm. wide and 2 cm. long extending along the tepal midrib from the end portion of the nectary; and the base portion of each petal adjacent the end of its nectary is heavily spotted with medium to large sized deep magenta maculae.

*Color change.*—As the flower ages, the color intensifies slightly and may become more golden toned under low light levels.

*Longevity.*—Tepals stay on the stem about three weeks.

Pedicels:

*Length.*—About 4 to 6 cm.

*Form.*—Sturdy and upright.

*Color.*—Medium green.

Fragrance: None.

Lasting quality: The flower is long lasting, both on the plant and as a cut flower.

Disease resistance: The flower and plant are resistant to disease, and in particular, they are resistant to Fusarium and Botrytis.

REPRODUCTIVE ORGANS

Stamens:

*Number.*—Six.

*Arrangement.*—Typical of genus Lilium.

Anthers:

*Color.*—Greyed Gold, R.H.S. 167A.

Filaments:

*Length.*—About 5 cm.

*Color.*—Ivory or yellow.

Pollen:

*Color.*—Greyed Gold, R.H.S. 167A.

Pistils:

*Number.*—One.

*Length.*—About 5 cm.

Stigma: Light plum to gold in color.

Ovary: Typical of genus Lilium.

THE FRUIT

Fertility: The fruit is fertile.

Shape: Ovoid.

Color at Maturity: Soft brown, sometimes overlaid with light plum.

This new variety of Asiatic hybric lily most nearly resembles the cultivar "Connecticut King" but it has much broader petals with heavy maculation, is much taller, and is superior for year around forcing. This new variety flowers somewhat later than "Connecticut King" but inbetween the flowering times of its siblings which have been selected for commercial cut-flower production, so the new variety broadens the cut-flower season for this type of lily.

Distinguishing Characteristics of Siblings
From the Cross *Lilium Wilsonii* var. *flavum* x "Connecticut King"

| Cv | Days to Bloom | Buds | Maculation |
|---|---|---|---|
| Pollyanna Serial No. 710,427 | 80–85 | 5–8 | Heavy, large. |
| Joanna Serial No. 710,457 | 80 | 5–7 | Light |
| Adelina Serial No. 710,614 | 80–85 | 6–8 | Very few and small. Of deep magenta color. |
| Vanessa Serial No. 710,496 | 90–95 | 5–8 | Very light |
| Yolanda Serial No. 710,577 | 95–100 | 5–8 | Sparse and of deep magenta color. |
| Gold Medal (Half Sib) Serial No. 710,592) | 60–70 | 6–8 | Few, tiny |

| Cv | Other Notable Characteristics |
|---|---|
| Pollyanna Serial No. 710,427 | Relatively narrow, widely spaced tepals and sepals with very little marginal overlapping. Arrangement, hexagonal. |
| Joanna Serial No. 710,457 | Tepal-sepal angle 60°. Arrangement, generally imbricated. |
| Adelina Serial No. 710,614 | Tepals are large, thick textured, relatively broad, and with lightly recurved tips. Arrangement, imbricated. |
| Vanessa Serial No. 710,496 | Tepals have slightly recurved tips and inconspicuous maculation. Arrangement, uniformly imbricated. |
| Yolanda Serial No. 710,577 | Larger bulb, flower dished with tepal-sepal angle 60°, with lightly overlapping arrangement. |
| Gold Medal (Half Sib) Serial No. 710,592) | Very thick and broad tepals in 60° overlapping arrangement with sepals, Unusually long lasting flowers, bud blast resistant when forced, and attains large bulb size only in season. |

I claim:

1. A new and distinctive variety of Asiatic hybrid lily, substantially as herein shown and described, characterized by its unique midseason time of flowering, and in particular, its unique yellow and gold flower color pattern and its heavy maculation; its vigorous growth and propagation character; and its versatility both as a garden plant and as a plant produced from precooled bulbs forced for cut-flower production.

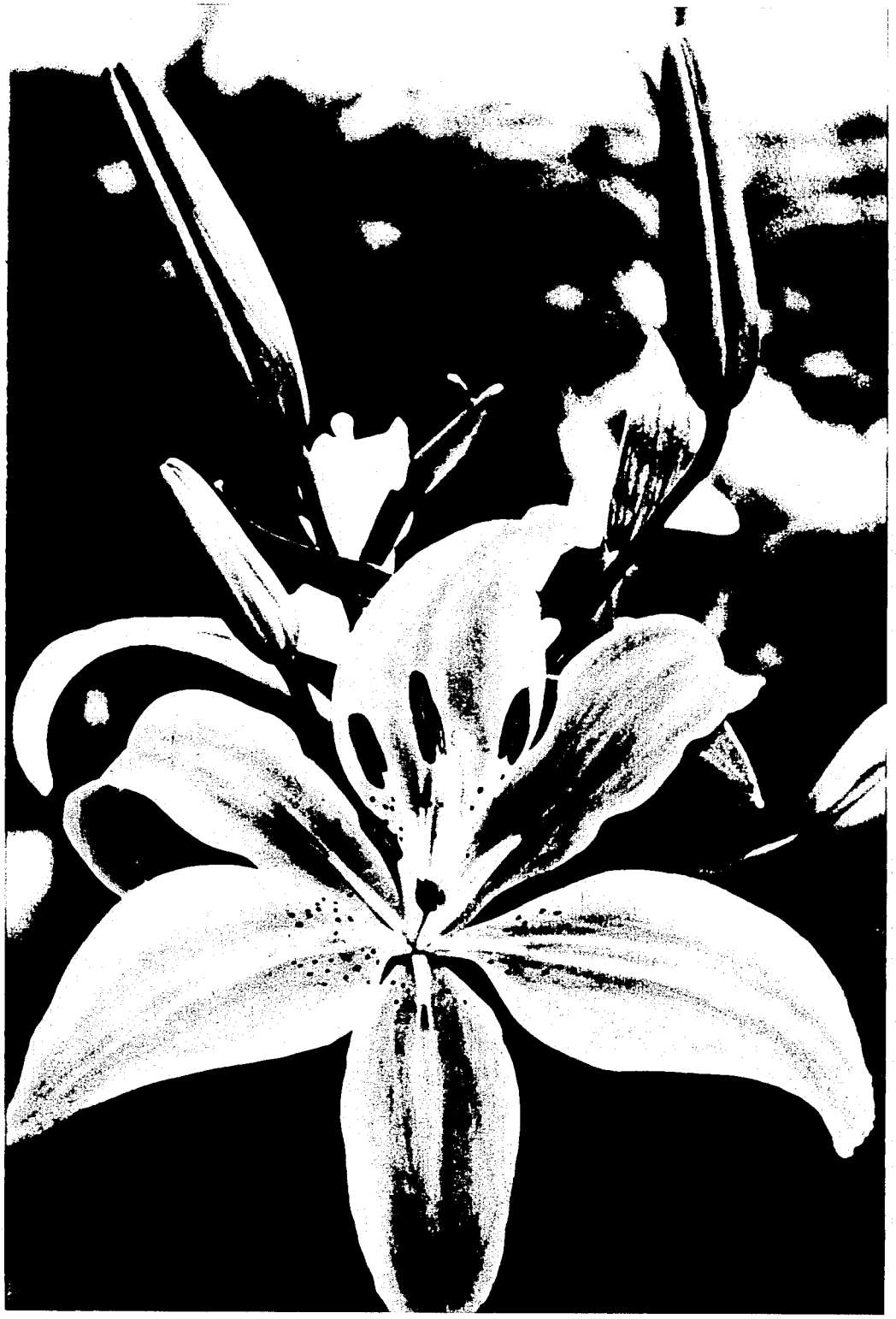

* * * * *